(12) United States Patent
Hodorek

(10) Patent No.: US 7,291,169 B2
(45) Date of Patent: Nov. 6, 2007

(54) CARTILAGE IMPLANT

(75) Inventor: Robert A. Hodorek, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 253 days.

(21) Appl. No.: 11/107,766

(22) Filed: Apr. 15, 2005

(65) Prior Publication Data

US 2006/0235517 A1   Oct. 19, 2006

(51) Int. Cl.
*A61F 2/30* (2006.01)
*A61F 2/38* (2006.01)

(52) U.S. Cl. ............... 623/14.12; 623/20.32; 623/18.11

(58) Field of Classification Search .. 623/11.11–14.12, 623/16, 18.11; 622/20.32
See application file for complete search history.

(56) References Cited

U.S. PATENT DOCUMENTS

| | | | | |
|---|---|---|---|---|
| 6,077,989 | A * | 6/2000 | Kandel et al. | 623/13.17 |
| 6,562,073 | B2 * | 5/2003 | Foley | 623/17.11 |
| 7,083,648 | B2 * | 8/2006 | Yu et al. | 623/15.11 |
| 2005/0251268 | A1 * | 11/2005 | Truncale | 623/23.63 |
| 2006/0235542 | A1 * | 10/2006 | Hodorek et al. | 623/23.51 |

* cited by examiner

*Primary Examiner*—Suzette Gherbi
(74) *Attorney, Agent, or Firm*—Baker & Daniels LLP

(57) ABSTRACT

A cartilage implant for replacing a portion of the cartilage adjacent to a skeletal joint is presented.

20 Claims, 1 Drawing Sheet

CARTILAGE IMPLANT

FIELD OF THE INVENTION

The invention relates to cartilage implants for skeletal joints.

BACKGROUND

Adjacent bones of the skeleton form connections called joints. These joints typically include one or more types of cartilage to reduce friction and impart flexibility. Hyaline cartilage, also known as articular cartilage, covers the joint surfaces of the bones and presents a smooth, slippery surface which facilitates the smooth relative motion of the bones. Hyaline cartilage has some elasticity and may provide some cushioning of percussive loads on the joints.

Fibrocartilage is an extremely resilient tissue and is also present at skeletal joints. In some joints, it provides great strength while allowing some movement as in the intervertebral disks and in the interpubic joint. In freely movable joints, where the surfaces are completely separated, the bones forming the joint may be separated by fibrocartilaginous plates or menisci. Menisci are found in the temporomandibular, stemoclavicular, acromioclavicular, wrist, and knee joints. The menisci fill the gap between the opposing bones at various positions of their articulation, increase the depth of engagement of the articular surfaces to increase joint stability, ease gliding movements, distribute joint pressure, and attenuate shock to the joint.

For example, the meniscus of the knee joint is a half moon shaped piece of cartilage that lies between the weight bearing joint surfaces of the femur and the tibia. It is triangular in cross section and is attached to the lining of the knee joint along its periphery. There are two menisci in a normal knee; the outer one is called the lateral meniscus, the inner one the medial meniscus. The menisci play an important role in absorbing impact loads. Complete removal of a meniscus can result in progressive arthritis in the joint.

The various cartilages of the joints are subject to damage due to traumatic injury, aging, and disease. Various repairs and replacements have been used to relieve pain and restore function to the joint where the cartilage has been damaged. For example hyaline cartilage may be damaged by impact injuries or worn down in the course of arthritis. Typically, the ends of the bones forming a joint are cut away and replaced with prosthetic bearings made of metal and plastic to restore pain free articulation of the joint. In cases where the damage occurs as a small localized defect, some investigators have attempted to replace only the small defect by placing a patch of replacement material, natural or synthetic, at the defect.

Fibrocartilage is often damaged by traumatic motion injuries such as automobile accidents and sports and job related injuries. For example, tears to the meniscus of the knee often result from a sudden load being applied to the meniscal tissue which is severe enough to cause the meniscal cartilage to fail and let go. This usually occurs from a twisting injury or a blow to the side of the knee that causes the meniscus to be levered and compressed against the bone. However, fibrocartilage may also be damaged due to degeneration. For example, degenerative meniscal tears are a failure of the meniscus over time. There is a natural drying out of the meniscus that progresses with age. The meniscus becomes less elastic and compliant and as a result may fail with only minimal trauma including during activities of daily living such as squatting and bending. Fibrocartilage repairs include suturing or replacement of the damaged tissues.

SUMMARY

The present invention provides a cartilage implant for replacing a portion of the cartilage adjacent to a skeletal joint.

In one aspect of the invention, a cartilage implant for replacing a portion of the cartilage adjacent to a skeletal joint includes a bearing portion for contacting opposing surfaces of the joint and a flexible drape extending from the bearing portion to anchor the bearing portion adjacent to the joint.

In another aspect of the invention, fasteners are insertable through the drape and the drape includes a reinforced periphery to resist the fasteners tearing through the drape.

In another aspect of the invention, the bearing portion and the drape each form at least a portion of a ring. The bearing portion forming a relatively more complete ring than the drape.

In another aspect of the invention, the bearing portion and the drape each form at least a portion of a ring. The bearing portion forming a relatively less complete ring than the drape.

In another aspect of the invention, the bearing portion includes an annular wall having a generally triangular cross section tapering from a relatively narrow top rim to a relatively broad bottom surface.

In another aspect of the invention, the annular wall includes a bearing surface that is concave upward.

In another aspect of the invention, the drape includes a tissue contacting portion including tissue growth promoting substances.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Figure 1:
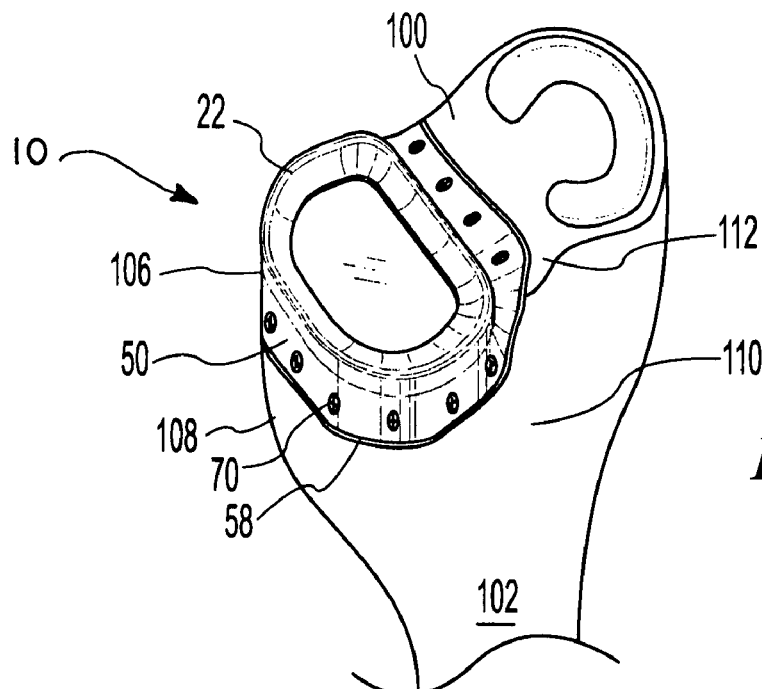
FIG. 1 is a perspective view of an implant according to the present invention.

Embodiments of a cartilage implant include a bearing portion and a peripheral drape for mounting the implant adjacent a surgical site. The cartilage implant may function as a replacement for damaged or diseased cartilage of a skeletal joint to sustain continued joint function. The cartilage implant may be used to replace a portion of any skeletal joint including, but not limited to, joints of the hip, knee, shoulder, spine, elbow, wrist, ankle, jaw, and digits. The implant may be configured to replace a relatively small defect within the joint, an entire compartment of the joint, and/or the total joint. For example, an implant for a knee may be configured to replace a defect in the hyaline cartilage of the femur, tibia, or patella. In another example, an implant for a knee may be configured to replace all or part of a fibrocartilage meniscus.

The bearing portion may be made of any material, both natural and synthetic, suitable for articulation within a joint.

Preferably the bearing material is resilient to cushion the joint. The bearing material may also permit intraoperative cutting or other shaping of the bearing portion to fit a surgical site. For example, the bearing material may be shapeable by cutting with scissors. The bearing portion may include natural tissues including hyaline cartilage, fibrocartilage, and/or other natural tissues. The bearing portion may include synthetic materials including metals, ceramics, polymers, and/or other suitable synthetic materials. A polymer bearing may include polyolefins, polyesters, polyimides, polyamides, polyacrylates, polyketones, and/or other suitable polymers. For example the bearing portion may include ultrahigh molecular weight polyethylene.

The bearing portion may include a hydrogel having a three dimensional network of polymer chains with water filling the void space between the macromolecules. The hydrogel may include a water soluble polymer that is crosslinked to prevent its dissolution in water. The water content of the hydrogel may range from 20-80%. The high water content of the hydrogel results in a low coefficient of friction for the bearing due to hydrodynamic lubrication. Advantageously, as loads increase on the bearing component, the friction coefficient decreases as water forced from the hydrogel forms a lubricating film. The hydrogel may include natural or synthetic polymers. Examples of natural polymers include polyhyaluronic acid, alginate, polypeptide, collagen, elastin, polylactic acid, polyglycolic acid, chitin, and/or other suitable natural polymers and combinations thereof. Examples of synthetic polymers include polyethylene oxide, polyethylene glycol, polyvinyl alcohol, polyacrylic acid, polyacrylamide, poly(N-vinyl-2-pyrrolidone), polyurethane, polyacrylonitrile, and/or other suitable synthetic polymers and combinations thereof.

The drape provides for flexible fixation of the cartilage implant within the joint. The drape may include woven fabrics, non-woven fabrics, films, and/or other suitable flexible materials. The drape may include the same or different materials as the bearing portion. For example the drape and bearing portion may be formed of the same material in a unitary construction such as by molding in one piece a bearing portion and continuous drape. In another example, the drape and bearing portion are separate parts joined together. The drape may be attached to the bearing portion by bonding, mechanical fasteners, porous interdigitation, ultrasonic welding, and/or by any other suitable attachment mechanism. Bonding may include heat bonding, adhesive bonding, chemical bonding, and/or other forms of bonding. Mechanical fasteners may include screws, pins, staples, sutures, and/or other suitable fasteners. For example, the bearing portion may be molded adjacent a porous fabric drape such that the bearing portion material interdigitates into the fabric pores to join the drape to the bearing portion.

The drape may be made of any material, natural and synthetic, suitable for implantation. Preferably the drape is flexible to permit some movement of the bearing portion. The drape material may also permit intraoperative cutting or other shaping of the drape to fit a surgical site. For example the drape may be intraoperatively shapeable by cutting with scissors. The drape may include natural tissues including fibrocartilage, fascia, pericardium, and/or other natural tissues. The drape may include synthetic materials including metals, polymers, ceramics, hydrogels and/or other suitable materials. A polymer drape may include resorbable and/or non-resorbable polymers. Examples of resorbable polymers include polylactic acid polymers, polyglycolic acid polymers, and/or other suitable resorbable polymers. Examples of non-resorbable polymers include polyolefins, polyesters, polyimides, polyamides, polyacrylates, polyketones, and/or other suitable non-resorbable polymers. A metal drape may include titanium, tantalum, stainless steel, and/or other suitable metals and alloys thereof. For example metal fibers may be woven into a porous flexible drape.

The drape may be attached to the hard and/or soft tissues of a joint by mechanical fasteners, adhesives, tissue ingrowth, and/or other suitable attachment mechanism. The attachment mechanism may be permanent and/or bioabsorbable. For example the drape may be screwed, pinned, sutured, or stapled to the bone and/or soft tissue adjacent the joint. The drape may include preformed openings for receiving fasteners. The drape may include a reinforced edge to strengthen the drape against pullout of fasteners. For example, the edge may be reinforced by hemming, molding, braiding, embedding a cord, and/or by other suitable reinforcement mechanism. The reinforced edge may form a thicker portion of the drape.

The bearing portion may be formed by casting, injection molding, compression molding, machining, and/or other suitable forming processes and combinations thereof. For example, the bearing portion may be molded onto a porous flexible drape such that the bearing portion interdigitates with the drape and is thereby joined to it.

The drape and/or bearing portion may include tissue contact surfaces configured for enhanced fixation to tissue. For example the tissue contact surfaces may be porous, have a high friction surface, and/or incorporate tissue growth promoting substances. The tissue contact surface may be coated with or otherwise incorporate calcium ceramics, tissue growth factors, porous metals, and/or other suitable tissue fixation enhancing substances.

The tissue contact surface and/or drape may be adhered to adjacent tissue with a biocompatible adhesive. Examples of biocompatible adhesives include fibrin glue, cyanoacrylate adhesive, epoxy, polymethylmethacrylate, and/or other suitable adhesives.

Figure 2:
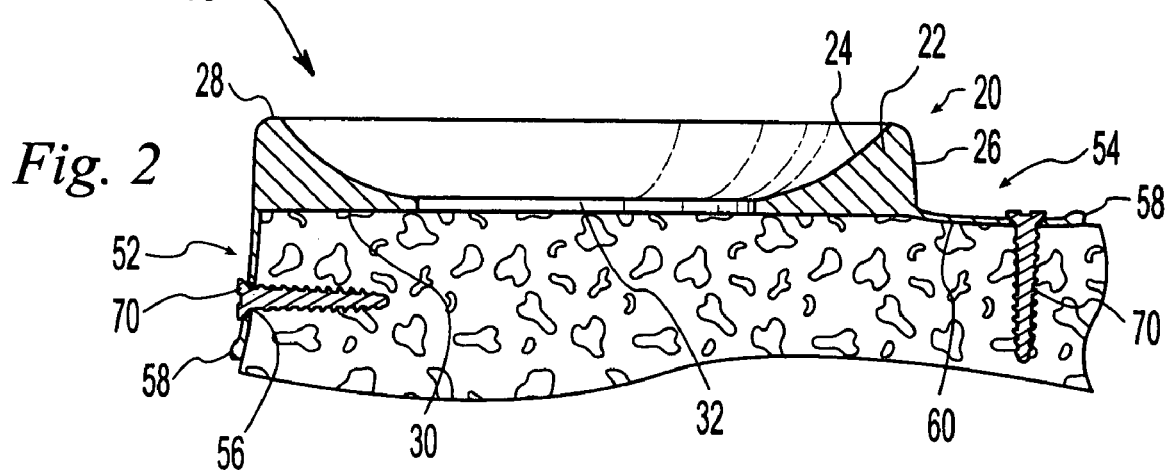
FIG. 2 is a sectional view taken along line 2-2 of FIG. 1.
Figure 3:
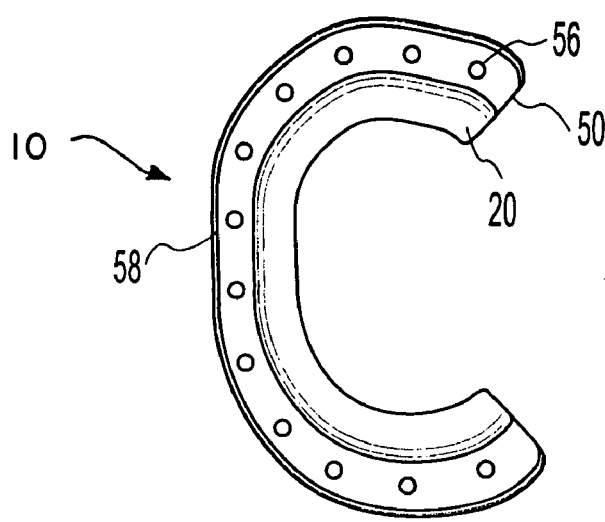
FIG. 3 is a top plan view of the implant of FIG. 1 showing the implant cut to a smaller size.

FIGS. 1-3 depict an illustrative example of a cartilage implant 10 according to the present invention. The illustrative implant 10 is in the form of a lateral meniscus implant for a knee joint. The implant 10 is attached to the proximal end 100 of the tibia 102 adjacent to the knee joint. However, it is within the scope of the invention for the cartilage implant 10 to be configured to replace fibrocartilage, hyaline cartilage, or other cartilage. Likewise, it is within the scope of the invention for the cartilage implant to replace a small portion of joint cartilage, to replace an entire compartment of a joint, to replace multiple compartments of a joint, and/or to replace any amount of any cartilage component in any skeletal joint. The illustrative implant 10 includes a bearing portion 20 having an annular wall 22 forming a cup shaped body with an inner convex-upward bearing surface 24, an outer surface 26, a top rim 28, and a bottom surface 30. The bearing portion is shaped like a natural meniscus having a generally triangular cross section tapering from a relatively narrow top rim 28 to a relatively broad bottom surface 30. The annular wall 22 forms a ring that is open in the center 32 to allow the hyaline cartilage of the proximal tibia 102 to articulate with the femur. The inner bearing surface 24 is curved so that it is concave upward to better receive and conform to the periphery of the femoral condyle. The bearing portion 20 preferably includes a resilient polymer such as a PVA hydrogel.

The implant 10 further includes a drape 50 for securing the implant 10 adjacent to the knee joint. The drape 50 preferably includes a flexible sheet extending from the outer surface 26 of the bearing portion 20. The drape 50 may be extended over adjacent tissues and connected to the tissues to hold the implant in place while permitting some anatomic movement of the bearing portion 20. As seen in FIGS. 1 and 2, a first portion 52 of the drape is extended generally vertically downwardly over the anterior 106, lateral 108, and posterior 110 sides of the tibia 102 and a second portion 54 is flexed outwardly and extended generally horizontally over the intercondylar portion 112 of the proximal tibia 102. The drape 50 is formed as a continuous, but thinner, extension of the bearing portion 20. The drape 50 is attached to the bone with screws 70 inserted through the drape 50 and into the bone. The drape 50 may include preformed openings 56 for receiving the screws 70 or the screws 70 may be pierced through the drape 50. The drape 50 includes a thickened outer edge 58 to strengthen the edge 58 against tearing around the screws 70. The illustrative implant is made by molding the bearing portion 20 with a continuous drape 50 and thickened outer edge 58 in a single operation. The fastener openings 56 are punched into the drape 50 after molding.

Preferably the screws 70 are made of a resorbable polymer, such as polylactic acid, so that they are eventually metabolized by the patient's body. The drape 50 is preferably porous to act as a tissue scaffold for promoting ongrowth and/or ingrowth of the soft tissues surrounding the knee joint. The long term attachment of the drape 50 may be further enhanced by coating the tissue contact surfaces 60 with tissue growth promoting substances, such as growth factors. The initial attachment of the drape 50 may be enhanced by using biocompatible adhesives, such as fibrin glue, between the tissue contacting portions 60 and the underlying tissue.

The implant 10 may be provided as a complete ring as shown in FIG. 1, or it may be provided as a partial ring as shown in FIG. 3. The bearing portion 20 and drape 50 do not have to have the same ring shape. For example, the drape 50 can form a relatively more complete ring while the bearing portion 20 forms a relatively less complete ring to provide more fixation area for the drape 50 while presenting an anatomical "C"-shaped bearing portion 20. Alternatively, the bearing portion 20 may form a relatively more complete ring while the drape 50 forms a relatively less complete ring where, for example, it is desired to avoid placing the drape 50 in the intercondylar region 112. For example, it may be desirable to avoid disturbing the insertions of the cruciate ligaments in the intercondylar region 112.

Although examples of a cartilage implant and its use have been described and illustrated in detail, it is to be understood that the same is intended by way of illustration and example only and is not to be taken by way of limitation. The invention has been illustrated in the context of a tibial meniscal implant. However, the cartilage implant may be configured in other shapes and for use at other locations within a patient's body. Accordingly, variations in and modifications to the cartilage implant and its use will be apparent to those of ordinary skill in the art, and the following claims are intended to cover all such modifications and equivalents.

What is claimed is:

1. A cartilage implant for replacing a portion of the cartilage adjacent to a skeletal joint, the implant comprising:
   a bearing portion for contacting opposing surfaces of the joint, the bearing portion including an annular wall forming at least a portion of a ring; and
   a flexible drape extending from the bearing portion to anchor the bearing portion adjacent to the joint, the drape forming at least a portion of a ring, wherein the bearing portion forms a relatively less complete ring than the drape.

2. The implant of claim 1 wherein the annular wall comprises a generally triangular cross section tapering from a relatively narrow top rim to a relatively broad bottom surface.

3. The implant of claim 1 wherein the bearing portion comprises a hydrogel.

4. The implant of claim 1 wherein the drape further comprises a tissue contacting surface configured for enhanced fixation.

5. The implant of claim 4 wherein the tissue contacting surface comprises tissue growth promoting substances.

6. The implant of claim 1 wherein the annular wall includes a bearing surface that it is concave upward.

7. A cartilage implant for replacing a portion of the cartilage adjacent to a skeletal joint, the implant comprising:
   a bearing portion for contacting opposing surfaces of the joint, the bearing portion including an annular wall forming at least a portion of a ring, the annular wall having a generally triangular cross section tapering from a relatively narrow top rim to a relatively broad bottom surface; and
   a flexible drape extending from the bearing portion to anchor the bearing portion adjacent to the joint.

8. The implant of claim 7 wherein the annular wall includes a bearing surface that it is concave upward.

9. The implant of claim 7 wherein the drape further comprises a tissue contacting surface configured for enhanced fixation.

10. The implant of claim 9 wherein the tissue contacting surface comprises tissue growth promoting substances.

11. The implant of claim 7 wherein the drape further includes a reinforced periphery.

12. The implant of claim 7 wherein the bearing portion comprises a hydrogel.

13. A cartilage implant for replacing a portion of the cartilage adjacent to a skeletal joint, the implant comprising:
   a bearing portion for contacting opposing surfaces of the joint, the bearing portion defining a body having an upwardly convex bearing surface and an outer surface, the body having a generally triangular cross section; and
   a flexible drape extending from the bearing portion to anchor the bearing portion adjacent to the joint, wherein the implant is in the form of a meniscus for a knee joint.

14. The implant of claim 13 wherein the bearing portion forms a complete ring.

15. The implant of claim 13 wherein the bearing portion forms an incomplete "C"-shaped body.

16. The implant of claim 13 wherein the drape extends outwardly from the outer surface drape.

17. The implant of claim 16 further comprising a plurality of screws engageable with the drape.

18. The implant of claim 13 wherein the drape further comprises a tissue contacting surface configured for enhanced fixation.

19. The implant of claim 18 wherein the tissue contacting surface comprises tissue growth promoting substances.

20. The implant of claim 13 wherein the drape further includes a reinforced periphery.

* * * * *